US00PP08287P

United States Patent [19]

Trees

[11] Patent Number: Plant 8,287

[45] Date of Patent: Jun. 29, 1993

[54] GERANIUM PLANT — BSR-284 PINK CULTIVAR

[75] Inventor: Scott C. Trees, Arroyo Grande, Calif.

[73] Assignee: George J. Ball, Inc., West Chicago, Ill.

[21] Appl. No.: 761,706

[22] Filed: Sep. 18, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Assistant Examiner*—E. F. McElwain
*Attorney, Agent, or Firm*—Burns, Doane, Swecker & Mathis

[57] ABSTRACT

A new and distinct tetraploid *Pelargonium*×*hortorum* cultivar named BSR-284 Pink is provided. This new Zonal Geranium cultivar was the result of a controlled breeding program wherein the TWIST cultivar (U.S. Plant Pat. No. 5,928) was pollinated by the Sunbelt Coral cultivar (U.S. Plant Pat. No. 5,757). The new cultivar forms attractive semi-double pink florets which contrast well with dark green foliage. The leaf edges are darker than the centers of the leaves on the upper surface. The upper two petals of the florets commonly include a white eye. The attractive dark green foliage coloration exhibits improved tolerance to stress during shipment. The growth habit is inherently compact and self-branching and does not require the use of growth regulators to maintain such growth characteristic. Good tolerance to wind and rain also is exhibited.

1 Drawing Sheet

SUMMARY OF THE INVENTION

The present invention comprises a new and distinct Geranium cultivar, botanically known as *Pelargonium*-×*hortorum*, and hereinafter is referred to by the cultivar name BSR-284 Pink.

The new cultivar is the product of a planned breeding program which had as its objective the creation of a highly productive new Geranium cultivar which exhibits attractive blossoms, dark green foliage, a compact self-branching growth habit, no requirement for the use of a growth regulator, a propensity for rapid rooting, and improved foliar tolerance to stress during shipment. This objective was satisfactorily fulfilled in the cultivar of the present invention.

The breeding program which resuled in the production of the new cultivar of the present invention was carried out in a controlled environment during 1989 at Santa Maria, Calif., U.S.A. The female parent (i.e., the seed parent) was the TWIST cultivar (U.S. Plant Pat. No. 5,928). Such female parent formed semi-double coral-melon florets, formed dark green foliage, and was compact. The male parent (i.e., the pollen parent) was the Sunbelt Coral cultivar (U.S. Plant Pat. No. 5,757). Such male parent was vigorous and large-umbelled, formed semi-double coral-orange florets, formed medium green foliage, and exhibited good field performance. The parentage of the new cultivar can be summarized as follows:

TWIST×SUNBELT CORAL.

The seeds resulting from the above pollination were sown and plantlets were obtained which were physically and biologically different from each other. Selective study which was finalized on Jan. 20, 1990, at Santa Maria, Calif. resulted in the identification of a single plant of the new cultivar. This plant initially was designated BSR-284.

It was found that the new cultivar of the present invention:

(a) exhibits attractive pink semi-double florets, wherein the two upper petals commonly possess a white eye on the upper surface,
(b) forms attractive dark green foliage which exhibits improved tolerance to stress during shipment,
(c) bears leaves wherein the edges of the upper surface tend to be darker than the central portions, and
(d) exhibits an inherently compact and self-branching growth habit in the absence of growth regulators.

Asexual reproduction of the new cultivar by vegetative cuttings initially taken on Feb. 12, 1990, and horticulturally examined in a controlled environment on Apr. 15, 1990, at Santa Maria, Calif., has demonstrated that the characteristics of the new cultivar as herein described are firmly fixed and are retained through successive generations of asexual propagation.

When plant material of the BSR-284 Pink cultivar is subjected to standard random amplified polymorphic DNA marker analysis (RAPD) using polymerase chain reaction (PCR) and a known set of DNA primers, it is found to exhibit a distinctive fingerprint map which is on file at the Ball Flora Plant Division of George J. Ball, Inc. at Arroyo Grande, Calif.

BSR-284 Pink has not been observed under all possible environmental conditions to date. Accordingly, it is possible that the phenotype may vary somewhat with variations in the environment, such as temperature, light intensity, and day length.

When the new cultivar of the present invention is compared to the Satisfaction Hot Pink cultivar, the BSR-284 Pink cultivar is found to exhibit a considerably lighter floret coloration on the upper surface of the petals. The foliage coloration of the BSR-284 Pink cultivar tends to be darker than that of the Satisfaction Hot Pink cultivar. Also, the corolla diameter of the BSR-284 Pink cultivar tends to be slightly smaller than that of the Satisfaction Hot Pink cultivar as specified in greater detail hereafter.

The new cultivar of the present invention is being marketed under the SHOWCASE trademark.

BRIEF DESCRIPTION OF THE PHOTOGRAPH

The accompanying photograph shows as nearly true as it is reasonably possible to make the same in a color illustration of this charaacter, a typical specimen of an overall plant of the new cultivar. The plant was grown in a greenhouse at Santa Maria, Calif.

DETAILED DESCRIPTION

The chart used in the identification of colors described herein is The R.H.S. Colour Chart of The Royal Horticultural Society, London, England. Color terminology in common terms sometimes precedes the reference to The R.H.S. Colour Chart information. The color values were determined on Jul. 31, 1991 between 3:00 to 4:00 p.m. using a light intensity of 680 footcandles at Santa Maria, Calif. The plants described were grown under standard greenhouse conditions.

Classification:

*Botanical.*—*Pelargonium*×*hortorum,* cv. BSR-284 Pink.

*Commercial.*—Zonal Geranium.

INFLORESCENCE

A. Umbel:

*Average diameter.*—Approximately 11 to 13 cm.

*Average depth.*—Approximately 5.5 to 6.0 cm.

*Peduncle length.*—Approximately 15 to 21 cm.

*Peduncle color.*—Green Group 141C. This compares to Green Group 143A for the SATISFACTION HOT PINK cultivar.

*Pedicel length.*—Approximately 3.75 to 4.0 cm.

*Pedicel color.*—Reddish-purple, Greyed-Purple Group 185C, over a green background.

When five month old plants are grown in the field, the BSR-284 Pink cultivar commonly possesses approximately 54 to 60 umbels per plant while the Satisfaction Hot Pink cultivar commonly possesses approximately 69 to 73 umbels per plant. Such field grown plants commonly possess approximately 35 to 37 florets per umbel for the BSR-284 Pink cultivar and approximately 59 to 62 florets per umbel for the Satisfaaction Hot Pink cultivar.

B. Corolla:

*Average diameter.*—Approximately 4.25 to 4.5 cm. This can be compared to approximately 4.5 to 4.7 cm. for the Satisfaction Hot Pink cultivar.

*Form.*—Semi-double, commonly 6 petals plus approximately 3 to 4 petaloids. The large petals commonly are non-imbricate and measure approximately 2.3 cm. in length and approximately 1.7 cm. in width, and the petaloids commonly are large and flat and are approximately 2.3 cm. in length and approximately 1.3 cm. in width. In contrast the florets of the Satisfaction Hot Pink cultivar commonly possess approximately 5 to 6 large imbricate petals which measure approximately 2.3 cm. in length and approximately 2.3 cm. in width, and 2 to 3 twisted petaloids which range from approximately 1.3 to 1.8 cm. in length. The petaloids of the BSR-284 Pink cultivar are much larger and flatter than those of the Satisfaction Hot Pink cultivar.

*Color (general tonality from a distance of 3 meters)*-.—Medium to light pink, Red-Purple Group 65A.

*Color (abaxial).*—Red-Purple Group 65A commonly with a white eye, White Group 155D, on the upper two petals. This compares to Red-Purple Group 57B for the Satisfaction Hot Pink cultivar, which also includes a similar white eye, White Group 155D, on the upper two petals.

*Color (adaxial).*—Red-Purple Group 65D. This compares to Red-Purple Group 68B shading to White Group 155D at the base of the petals for the Satisfaction Hot Pink cultivar.

C. Bud:

*Shape.*—Upright, in a hemispheroidal cluster.

*Color (abaxial).*—Red-Purple Group 57A with a white eye, White Group 155D.

*Color (adaxial).*—Red-Purple Group 73B.

D. Reproductive organs:

*Androecium.*—The anthers commonly are approximately 2.0 to 2.5 mm. in length at the opening of the bud. The pollen is orange in coloration, Orange-Red Group 33A, and the filaments often are petaloid.

*Gynoecium.*—The pistil length commonly is approximately 7 to 8 mm. on a five day-old floret; there is a single stigma which commonly branches into 4, 5 or 6 parts; and the style length is approximately 3 mm.

*Fertility.*—Is not self fertile. This can be contrasted to the Satisfaction Hot Pink cultivar which occasionally sets fruits under field growing conditions.

E. Spring flowering response period: Approximately 6 to 7 weeks from rooted cuttings under greenhouse conditions maintained at 55° F. at night and 72° F. during the day when potted on March 1st in a soil mix (e.g., Sunshine No. 2 brand soil mix) in 10 cm. pots.

F. Outdoor flower production: Substantially continuous.

G. Durability: Corolla shows tolerance to wind and rain.

PLANT

A. Foliage: Dark green with darker coloration at the edges of the leaves. The foliage is of a distinctly darker green than that of the Satisfaction Hot Pink cultivar. Also, the dark green foliage of the BSR-284 Pink cultivar exhibits a more stable chlorophyll and better withstands a tendency to break down during the shipping of cuttings when compared to the Satisfaction Hot Pink cultivar.

*Form.*—Reniform, cordate base.

*Margin.*—Slightly crenate.

*Color (abaxial).*—Dark green, Green Group 135A, at the outer margins or zones (e.g., at approximately the outer ⅔'s of the leaves), and Green Group 135B at the center of the leaves. This compares to Green Group 137A for the Satisfaction Hot Pink cultivar.

*Color (adaxial).*—Green Group 137B. This compares to a coloration of Green Group 138A for the Satisfaction Hot Pink cultivar.

*Tolerance to Botrytis blight.*—Some.

B. General Appearance and form:

*Internode length.*—Commonly varies from approximately 2 to 3 cm.

*Branching pattern.*—Freely basal branching. Is more compact than the Satisfaction Hot Pink cultivar when grown in the field. No pinching or the use of a growth regulator is required to obtain basal-branching plants. However, the Satisfaction Hot Pink cultivar does require pinching or the use of a growth regulaor to obtain branching.

*Height.*—Approximately 20 to 25 cm. above a 10 cm. pot when the blossoms first open.

I claim:

1. A new and distinct cultivar of Geranium plant named BSR-284 Pink, substantially as herein shown and described, which:

(a) exhibits attractive pink semi-double florets, wherein he two upper petals commonly possess a white eye on the upper surface, (b) forms attractive dark green foliage which exhibits improved tolerance to stress during shipment, (c) bears leaves wherein the edges of the upper surface tend to be darker than the central portions, and (d) exhibits an inherently compact and self-branching growth habit in the absence of growth regulators.

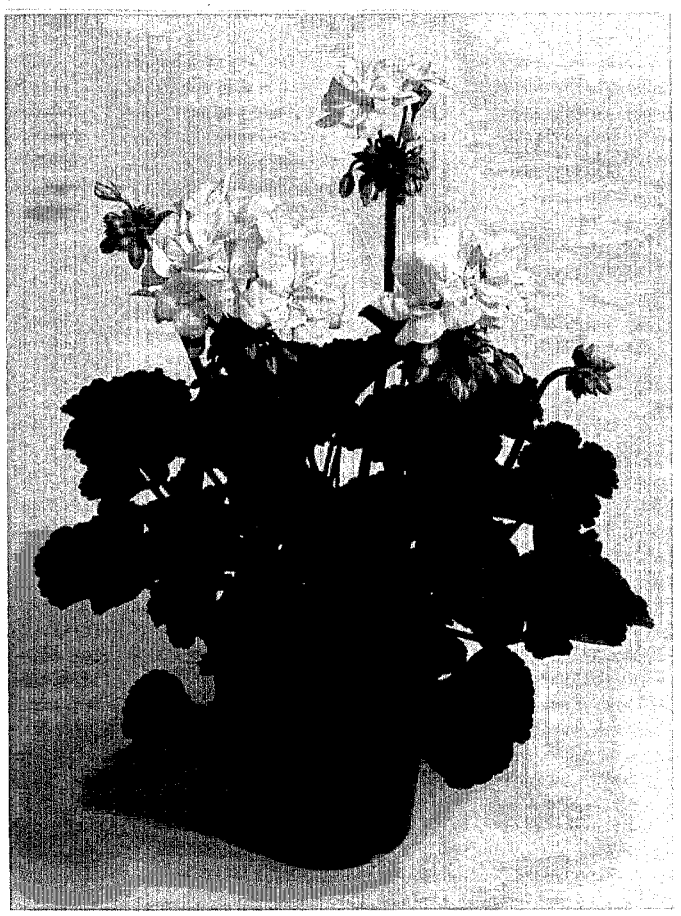

* * * * *